US00PP10721P

United States Patent [19]

Hammond

[11] Patent Number: Plant 10,721

[45] Date of Patent: Dec. 15, 1998

[54] *ARGYRANTHEMUM FRUTESCENS* 'CARMELLA'

[76] Inventor: Frank Hammond, 100 Boundary Road, Narre Warren East Victoria, 3804, Australia

[21] Appl. No.: 846,477

[22] Filed: May 1, 1997

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Kent L. Bell

[57] ABSTRACT

A new and distinct selection of Silver Flower which shall be referred hereinafter as *Argyanthemum frutescens* cultivar 'Carmella'. *Argyanthemum frutescens*cultivar Carmella differs distinctively from other *Argyanthemum frutescens* plants by its unique combination of consistent and uniform pink colored flowers varying only slightly with age and foliage which has a more grey hue.

1 Drawing Sheet

BACKGROUND OF THE INVENTION

This invention relates to a new and distinct selection of *Argyranthemum frutescens* (L.) Schutz-Bip., native to the Canary Islands and a member of the Compositae family. *Argyanthemum frutescens* cv. 'Carmella' was the result of a controlled breeding program. the seed parent was *Argyranthemum frutescens* cv. 'Blanche' and the pollen parent was *Argyanthemum frutescens* cv. 'Rollasons Red',. I selected this seedling in 1995. My discovery was made at 100 Boundary Road, Narre Warren East, Victoria, Australia. Selection was based on the consistent and uniform pink colored flowers and the grey green foliage. My new plant has been asexually reproduced by cuttings since the discovery in 1995 at 100 Boundary Road, Narre Warren Wast, Victoria, Australia and later at Monrovia Nursery Company, 18331 E. Foothill Boulevard, Azusa, Calif. Had this controlled hybridization not occured and the seedling not been discovered and propagated, it may have been lost to mankind. It is unlikely these particular select and favorable attributes of the plant could be conveyed to progeny through sexual reproducrion in the next generation. However, through extensive propagation by rooting of the plant it has been established that the novel exceptional characteristics of this plant are stable and reliably passed on to clonal specimens through asexual reproduction.

SUMMARY OF THE INVENTION

*Arhyranthemum frutescens* cv. 'Carmella' has a uniform and consistent flower size and color. The ray flowers are pink with the base a white color presenting a uniform white eye surrounding the disc. With age the flower color changes only slightly with the tips lightening and the original pink ray color present just above the white based ring. Overall the effect is a very consistent pink color on all the flowers. The height of *Argyranthemum frutescens* cv. 'Carmella' is taller than either of its parents but has more uniformity within its cultivar group than either parent. The average height of my selection of twenty random samples is 33.0cm with a 2.4cm deviation. Though this is 10.6cm taller than cultivar 'Rollasons Red', the pollen parent, my selection has more uniformity as the pollen parent has a larger deviation of 4.2cm in height. The seed parent cultivar 'Blanche' is 9.9cm shorter but has a larger deviation of 2.5cm. This application is co-pending with those of four other Argyranthemum selections. 'Primose Petite' (U.S. Plant Pat. application Ser. No. 08/848,790) differs significantly in having white ray florets. 'Annabel' (U.S. Plant Pat. application Ser. No. 08/851,475) differs significantly in having white florets. 'Blanche' (U.S. Plant Pat. application Ser. No. 08/846,476) differs significantly in having white ray florets and also in height as previously stated. The final selection 'Gretel' (U.S. Plant Pat. application Ser. No. 08/848,790) differs significantly as outlined below. 'Carmella' maintains a pink color band of Amaranth Rose whereas 'Gretel' has no pink on the outer basal line. 'Carmella' has a larger growth habit whereas 'Gretel' is smaller. 'Carmella' has ray florets which are similar in color on the upper surface and under surface whereas 'Gretel' has ray florets which are darker in color on the upper surface and lighter in color on the under surface.

My selection *Argyranthemum frutescens* has tolerated a −5 degree Celsius temperature which is equvalent to a U.S.D.A. hardiness zone seven with no harm or damage. Winter protection is necessary from heavy frost.

BRIEF DESCRIPTION OF ILLUSTRATION

The accompanying photograph shows the plant in flower. The flower color is very uniform and consistent with a slight fading as the inflorescence matures. The white basal ring surrounded by pink color is also prominently displayed. Ray floret colors illustrated may vary slightly from the actual plant coloration due to light reflectance.

BOTANICAL DESCRIPTION

Below is a detailed description of *Argyranthemum frutescens* cultivar 'Carmella', the color terminology is from the British Horticulural Color Charts. Measurements are based on 20 random samples taken in Australia.

Botanical description:

*Overall habit.*—Perennial, subshrub.

*Overall size.*—Slightly wider than tall. Height—33.0cm (± 2.4cm). Width—49.6.cm (± 2.3cm).

Bloom season in Austrila: Heaviest bloom in Spring for 10 weeks.

*Melbourne.*—6–8 months per year.

*Brisbane.*—4–6 months per year.

*Bloom lastingness.*—7–14 days per inflorescence.

Foliage:

*Arrangement.*—Alternate.

*Surface.*—Upper: glabrous. Lower: glabrous.

*Shape.*—Pinnatisect, primary segments 3 to 5.

*Margins.*—Deeply to lightly parted, lobes end with mucronulate tip.

*Size.*—Length: 56.3mm (±7.0mm). Width: 34.4mm (±5.3mm).

*Color.*—Upper leaf surface: Leek Green 000858 to Parsley Green 00962. Lower leaf surface: slightly lighter in color a Spinach Green 0960.

*Texture.*—Freshly, succulent.

*Stem coloration.*—Spinach Green 0960/3, lighter in color than foliage.

Inflorescences:

*Fragrance.*—Light, faint, sweet scent.

*Bud shape.*—Globose.

*Bud length.*—9mm to 10mm.

*Bud width.13* 8mm to 10mm.

*Bud color.13* Spinach Green 0960/1, paper like bracts Majolica Yellow 09 mixed with a tint of Garnet Brown 00918/3.

*Arrangement.*—Heterogamus capitula, 1 per peduncle.

*Diameter.*—3.5 to 4.cm.

*Peduncle length.*—9–11cm.

*Disc flower color.*—Chinese Yellow 606.

*Disc diameter.*—1.5cm (±2cm).

*Disc floret reproductive organs.*—pistillate and staminate organs are present.

*Ray floret number.*—Average 19 to 21.

*Ray floret aspect.*—flattened, varies from 90 to 120degrees.

*Ray floret aspect.*—ligulate.

*Ray floret length.*—16–18mm.

*Ray floret width.*—6–8mm.

*Ray floret color.*—Initial flowering Amaranth Rose 530 to Rodamine Pink 527/1on upper surface and under surface. Mature flowering: lightly fading with age to Amaranth Pink 530/3 to Rhodamine Pink 527/3 on upper surface and under surface .

*Basal line.*—White color maintained throughout flowering, outer side of white basal line holds pink color of Amaranth Rose 530.

*Ray floret reproductive organs.*—Pistillate organs are present.

Fruit: A 2–4 angled cypsela, 1 winged.

Disease resistance: The rust diseases of the genera Coleosporium and Cronartium are not known to occur on my selection in Australia.

I claim:

1. A new and distinct *Argyranthemum frutescens* plant substantially as shown and described which differs distinctively from other *Arhyranthemum frutescens* plants by its unique combination of consistent and uniform pink colored flowers varying only slightly with age and foliage which has a more grey hue.

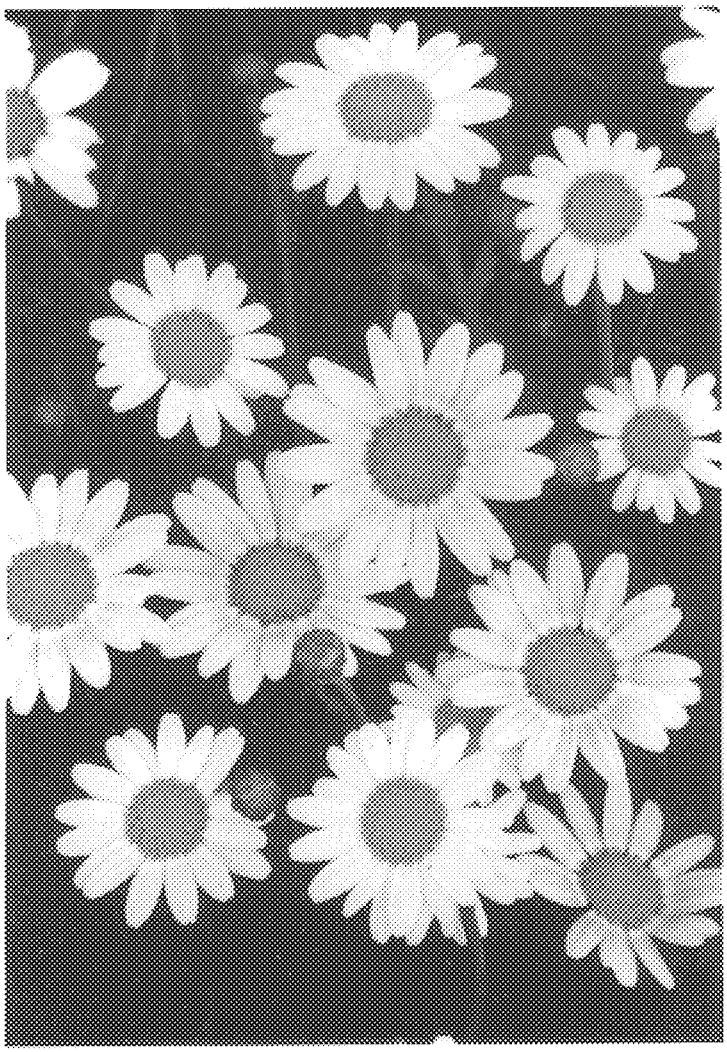

* * * * *